United States Patent [19]

Hewett et al.

[11] 4,156,694
[45] May 29, 1979

[54] BENZOBICYCLONONENE DERIVATIVES

[75] Inventors: Colin L. Hewett; David S. Savage, both of Glasgow, Scotland; James Redpath, Bishopbriggs, England; Thomas Sleigh, Wishaw, England; Duncan R. Rae, Lanark, England

[73] Assignee: Akzona Incorporated, Asheville, N.C.

[21] Appl. No.: 865,828

[22] Filed: Dec. 30, 1977

Related U.S. Application Data

[63] Continuation of Ser. No. 680,402, Apr. 26, 1976, abandoned.

[30] Foreign Application Priority Data

Apr. 29, 1975 [GB] United Kingdom ............... 17846/75

[51] Int. Cl.² ..................... C07C 87/40; C07C 91/16; C07C 87/28; A01N 9/20
[52] U.S. Cl. .................................. 260/571; 546/195; 544/381; 260/326.33; 260/326.8; 260/557 R; 260/558 D; 260/558 P; 260/559 R; 260/561 N; 260/562 R; 260/566 R; 260/570.8 R; 260/590 R; 568/633; 424/248.4; 424/251; 424/263; 424/274; 424/309; 424/311; 424/316; 424/324; 424/330; 544/106; 548/335; 568/660; 560/1; 560/255; 560/105; 560/20; 560/107; 560/73; 548/335
[58] Field of Search ............ 260/571, 576, 578, 501.1, 260/501.18

[56] References Cited

U.S. PATENT DOCUMENTS 3,976,696  8/1976  Freed et al. ..................... 260/571
4,008,277  2/1977  Hewett et al. ................... 260/571
4,076,953  2/1978  Freed et al. ................... 260/571 X

FOREIGN PATENT DOCUMENTS 41-18944  11/1966  Japan ..................... 260/576

Primary Examiner—Winston A. Douglas
Assistant Examiner—John Doll
Attorney, Agent, or Firm—Robert H. Falk; Charles A. Wendel; Francis W. Young

[57] ABSTRACT

The present invention relates to novel benzo(b) bicyclo[3.3.1]nones of the general formula I:

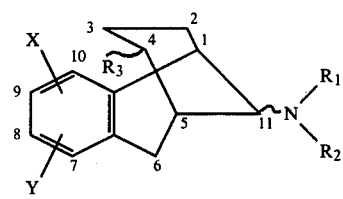

and a salt or nitrogen oxide thereof, in which $R_1$ and $R_2$ stand for hydrogen, alkyl of 1-6 carbon atoms, alkenyl of 1-6 carbon atoms, an optionally substituted aralkyl group or an acyl group or $R_1$ and $R_2$ together with the nitrogen atom represent a heterocyclic 5- or 6-membered ring $R_3$ is a free, etherified or esterified hydroxy, X and Y stand for hydrogen, hydroxy, halogen, alkyl or alkoxy of 1-6 C-atoms, nitro, $CF_3$ or an acyloxy group, having valuable biological activities, particularly anorectic activity.

8 Claims, No Drawings

BENZOBICYCLONONENE DERIVATIVES

This is a continuation of application Ser. No. 680,402, filed Apr. 26, 1976, now abandoned.

The present invention relates to novel biologically active tricyclic compounds, to processes for the preparation of these compounds and to the pharmaceutical application of these compounds. Particularly the invention relates to novel benzo(b) bicyclo[3.3.1]nonenes of the general formula I:

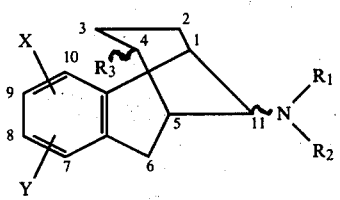

and a salt or nitrogen oxide thereof, in which $R_1$ and $R_2$ stand for hydrogen, alkyl of 1-6 carbon atoms, alkenyl of 1-6 carbon atoms, an optionally substituted aralkyl group or an acyl group or $R_1 + R_2$ together with the nitrogen atom represent a heterocyclic 5- or 6-membered ring $R_3$ is a free, etherified or esterified hydroxy, X and Y stand for hydrogen, hydroxy, halogen, alkyl or alkoxy of 1-6 C-atoms, nitro, $CF_3$ or an acyloxy group.

The compounds of the general formula I have valuable biological activities, particularly anorectic activity. Moreover the toxicity of the compounds is very low.

The compounds of the present invention may be prepared according to the usual methods described in the literature for similar compounds.

A very convenient starting product in the synthesis of the compounds of formula I is a substance of the general formula II:

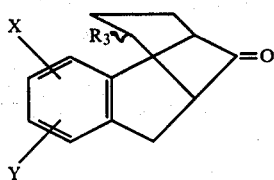

in which X, Y and $R_3$ have the meanings indicated previously.

These compounds II may be prepared in the usual manners starting from an optionally substituted (X and/or Y) β-tetralone. The tetralone in question, which is commercially available or can be prepared in a conventional manner from commercially available tetralones, is treated with pyrrolidine affording the corresponding 2-(pyrrolidino)enamine. The enamine is then converted with acrolein at low temperature into the corresponding 4-hydroxy-benzo(b)bicyclo[3.3.1]nonene-11-one. Alternatively the tetralone in question may be reacted directly with acrolein at elevated temperature in the presence of a tertiary amine such as trimethylamine to give the corresponding 4-hydroxy-benzo(b)bicyclo[3.3.1]nonene-11-one directly. The 4-hydroxy group of this compound may then optionally be etherified or esterified. The condensation of the 2-tetralone enamine with acrolein can be carried out at preferred temperatures from −60° to +25° C. in a variety of solvents, but best conditions use a low temperature of −50° to −45° C. for the addition of acrolein and allow the temperature to increase in a controlled manner to ambient temperature over a period of up to 3 hours.

The alternative direct condensation of the optionally substituted (X and/or Y) β-tetralone with acrolein can be carried out at preferred temperatures between +30° to +120° in a variety of solvents, but preferably at the boiling point of the solvent used, in the presence of a tertiary alkyl amine such as triethylamine or trimethylamine.

Starting from a compound of formula II the amines or amides of the invention I can be prepared most conveniently and directly by a reductive amination.

This method involves a reaction of the starting ketone II with formamide, N-alkylformamide or N,N-dialkylformamide or with an amine of the general formula III:

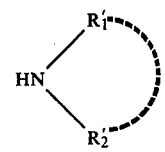

in which $R_1'$ and $R_2'$ have the same meanings as $R_1$ and $R_2$ with the exception of an acyl group, in the presence of a suitable reducing agent.

A reducing agent, that is very suitable for this reaction, is formic acid or a formic acid derivative such as a salt of formic acid and the amine of formula III. In the latter case the separate addition of the amine III is even superfluous. This reaction may be carried out at elevated temperature, preferably in the range of 80°–150° C., and most conveniently at the boiling point of the reaction mixture.

Other suitable reducing agents in this reaction are metal hydrides, such as lithiumaluminiumhydride, sodiumborohydride, sodiumtrimethoxyborohydride and diisobutylaluminiumhydride; an alkalimetal, preferably sodium, in an alcohol such as ethanol or isopropanol or hydrogen in the presence of a suitable catalyst, such as Raney nickel, Pt, $PtO_2$, Pd/C etc. Some reducing agents may remove the ether- or the ester group, optionally present at position 4, simultaneously to give compounds with a hydroxy group at position 4, such as $LiAlH_4$.

The compounds of the invention can further be obtained by reduction of the imino moiety of a compound of the general formula IV:

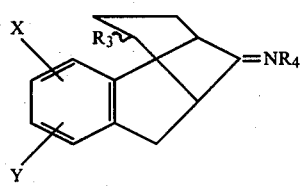

in which X, Y and $R_3$ have the meanings indicated above and $R_4$ stands for hydrogen, hydroxy, alkoxy, alkyl (1-6 C) or an optionally substituted aralkyl group.

The compounds of formula IV may be prepared by reaction of the ketone II with a primary amine of formula III $R_1'$=H) or with hydroxylamine or a hydroxylamine-alkylether under alkaline conditions in the usual manner for the preparation of imines or oximes.

The reduction of the imine IV is carried out under mild reaction conditions by means of standard procedures for the reduction of an imino-moiety. For example the reduction can be carried out by hydrogenation in the presence of a suitable catalyst, such as Raney nickel, Pt or PtO$_2$; with a metalhydride, particularly complex-metalhydrides derived from aluminium or boron, such as lithium-aluminiumhydride, dissolved or suspended in a suitable liquid, such as ether; with an alkalimetal preferably sodium in a suitable liquid such as ether, benzene or alcohol; or with sodiumamalgam or zinc dust in, for example, sodium hydroxide. The reaction may result simultaneously in a splitting off of the 4-ether or the 4-ester group to give the corresponding 4-alcohol, dependent upon the reducing agent used.

A third method for the preparation of the compounds according to the invention is starting from the hydroxyl compound of formula V:

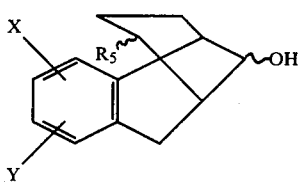

in which X and Y have the meanings indicated above and R$_5$ represents an etherified or esterified hydroxy group.

The compound V may be obtained by reduction of the corresponding ketone II under mild conditions so that the R$_5$ group present is not removed. A suitable reducing agent in this respect is sodiumborohydride.

The hydroxyl compound V can be converted into the corresponding amine in various way. For example, the said hydroxyl group may be converted into a suitable alkyl- or arylsulfonyloxy group (leaving group), such as a mesyloxy group, a tosyloxy group, a p-bromophenylsulfonyloxy group, a p-chlorophenylsulfonyloxy group, a p-nitrophenylsulfonyloxy group, etc. and then be reacted with an amine according to the general formula III.

Instead of the coversion of the hydroxy group into the above-mentioned alkyl- or arylsulfonyloxy group, the hydroxyl group may also be halogenated, for example with PCl$_5$, PBr$_3$, SOCl$_2$, etc., and then be converted into the desired compound I by reaction with the amine III.

The conversions from a hydroxyl group into an amino group are well-known and described in any chemical textbook.

The aforesaid primary reactions for the preparation of the compounds of the invention (I) may be followed by additional reactions for the conversion of a compound of formula I into a salt or nitrogenoxide thereof, or for the conversion from one compound of the invention into another compound of the invention.

So, it is possible to modify a substituent present at the phenylnucleus into another substituent within the definition of X and/or Y. For example, a methoxy group may be converted into a hydroxyl group, e.g. by treating with fused pyridine. HCl in the absence of a solvent or by hydrolysis with HBr; a hydroxy group can be converted into an alkoxy group, halogen, or an acyloxy group in a conventional manner.

The amines of the invention, unsubstituted or monosubstituted at the nitrogen atom (R$_1$ and/or R$_2$ is hydrogen) may be (ar)alkylated in the usual manner, for example by reacting the compound with an (ar)alkylhalide, or by acylating the compound followed by reduction of the carbonyl group.

For the introduction of methyl-groups at the nitrogen atom the well-known procedure of Eschweiler-Clarke (reaction with formaldehyde + formic acid) or the reaction with formaldehyde or haloformic esters, followed by reduction with e.g. sodiumcyanoborohydride is to be preferred.

An N-acyl derivative of the compounds according to the invention, may preferably be obtained by acylating a compound I, in which at least one of the groups R$_1$ or R$_2$ is hydrogen, in the usual manner using an anhydride or acid halide.

Such acylations, carried out on the 4-alcohol derivative I(in which R$_3$=OH), will result in simultaneous esterification of the 4-hydroxy group.

Where an N-formyl derivative is obtained directly from one of the aforesaid primary reactions, the amide in question may be hydrolysed using e.g. potassium or sodiumhydroxide to obtain the primary amine I. Such hydrolysis may result in a simultaneous hydrolysis of the 4-ester group to the 4-alcohol. For example, the reductive amination, in which the ketone II is reacted with formamide in the presence of formic acid (Leuckart-Wallach reaction) gives in first instance the N-formyl derivative I, which derivative can be hydrolysed to the primary amine I, or reduced to the corresponding N-methyl compound I.

An O-acyl derivative (R$_3$=acyloxy) of the compounds according to the invention in which the primary or secondary amine group remains unreacted may be prepared by treating the amine I, in which R$_3$=OH, with an acylating agent such as an acid halide or anhydride in the presence of a strong acid such as trifluoroacetic acid or perchloric acid.

All these additional conversions which might be carried out after the aforesaid primary reactions are standard procedures well-known in the art. As far as specific reagents have been mentioned in these additional conversions, it may be understood that these reagents can be replaced by other reagents, well-known in organic chemistry, having a similar effect as the specific reagents described.

The preparation of the ketone II used as starting product in the present synthesis to a compound of formula I results in a mixture consisting of two enantiomers of formula II in which the 4-alcohol or ester group is in the exo-position, and two enantiomers of formula II in which the 4-alcohol or ester group is in the endo-position. The exo-enantiomers can be separated from the endo-enantiomers by crystallisation or chromatography. Each of the racemic mixtures II thus obtained may be processed as such and then optionally resolved after conversion to a racemic compound I or may be resolved and then be processed into an optically active end product according to formula I.

The replacement of the oxo-group at position II of the ketone II with an amino group of the reduction of the imine IV introduces another asymmetric centre resulting in the mixture of two diastereomers I, in which the amino group is present in syn- or anti-position with respect to the benzene ring. The separate diastereomeric forms can be isolated from the mixture in the usual manner, for example by column chromatography, preparative thin-layer chromatography and/or fractional crystallisation.

The diastereomers, enantiomers and mixtures thereof of formula I as well as their preparation are also encompassed by this invention.

The novel compounds of formula I may be isolated from the reaction mixture in the form of a pharmaceutically acceptable salt, dependent upon the conditions in which the reaction is carried out. The pharmaceutically acceptable salts may also be obtained by treating the free base I with an organic or inorganic acid such as HCl, HBr, HI, $H_2SO_4$, $H_3PO_4$, acetic acid, propionic acid, glycollic acid, maleic acid, malonic acid, succinic acid tartaric acid, citric acid, benzoic acid, ascorbic acid, etc.

The term "alkyl" used in the definition of X, Y, $R_1$ and $R_2$ of the general formula I means a saturated branched or unbranched hydrocarbon radical with 1-6 carbon atoms, such as methyl, ethyl, n.propyl, n.butyl, cyclopropyl, cyclopropylmethyl, isopropyl, isobutyl, t.butyl, n.pentyl, isopentyl, cyclopentyl and hexyl. The same applies to the alkyl group present in the term "alkoxy" used in the definition of X and Y.

The term "alkenyl" used in the definition of $R_1$ and $R_2$ of the general formula I means an unsaturated branched or unbranched hydrocarbon radical with 2-6 carbon atoms such as vinyl, allyl and 3-methyl-but-2-enyl.

By "halogen" is preferably meant chlorine or bromine.

By an "aralkyl group", mentioned in the definition of $R_1$ and $R_2$, is meant an alkyl group with 1-6 carbon atoms, substituted with at least one aromatic group. Preferably a phenylalkyl group is meant, in which the alkyl group has 1-4 carbon atoms and in which the phenyl group may be substituted by one or more halogen, lower alkyl or alkoxy groups (1-4 C), such as benzyl, phenylethyl, phenylpropyl, phenylbutyl, 1-methyl-1-phenyl-ethyl, o-, m-, or p-anisyl, o-, m- or p-chlorobenzyl, veratryl, o-, m- or p-methyl-phenethyl or o-, m- or p-hydroxyphenethyl.

An "acyl group" mentioned in the definition of $R_1$, and $R_2$ means a group derived from an aliphatic, araliphatic or aromatic carboxylic acid. The aliphatic carboxylic acids cover acids with 1-18 carbon atoms, including a carbocyclic ring, and particularly those with 1-8 carbon atoms, such as acetic acid, propionic acid, butyric acid, iso-butyric acid, valeric acid, hexanoic acid, heptanoic acid, trimethyl-acetic acid, cyclopentane- or cyclohexane-carboxylic acid. The araliphatic or aromatic carboxylic acids cover unsubstituted as well as substituted araliphatic or aromatic carboxylic acids with 1-18 carbon atoms, especially the optionally substituted phenyl-carboxylic acids, and optionally substituted phenylalkyl-carboxylic acids, in which the alkyl group contains 1-4 carbon atoms and may be saturated as well as unsaturated, such as benzoic acid, o-, m- or p-toluic acid, o- or p-chlorobenzoic acid, p-methoxybenzoic acid, phenyl acetic acid, phenylpropionic acid, cinnamic acid, phenylbutyric acid, p-methylphenyl acetic acid, p-nitrobenzoic acid, etc.

The acyl group in the term "acyloxy" or "esterified hydroxy group" used in the definitions of X, Y and $R_3$ has a similar meaning.

The etherified hydroxy group mentioned in the definition of $R_3$ is an aliphatic (1-6 C) ether, a cycloaliphatic (5-10 C) ether, an aromatic ether, preferably a phenylether, an araliphatic ether, preferably a phenylalkylether, or a heterocyclic ether such as a tetrahydropyranylether. The phenyl moiety in the phenyl or phenylalkyl ethers may be substituted by alkyl (1-4 C), alkoxy (1-4 C), halogen or nitro.

The heterocyclic five- or six-membered rings, as mentioned in the definition of $R_1$ and $R_2$ (together with the nitrogen atom), are derived from 5- or 6-membered cyclic amines of formula III, such as pyrrole, pyrrolidine, pyrroline, piperidine, piperazine, imidazole or morpholine.

The nitrogen oxides of the compounds of the invention are prepared by oxidising a compound I with $H_2O_2$ or a peracid.

The novel compounds according to this invention as well as the pharmaceutically acceptable salts thereof have, as already said, valuable anorectic activities. A long term oral administration of the compounds I did not evoke tolerance to the anorectic effect. The compounds I, especially the 11-syn isomers I, show moreover a moderate anti-inflammatory activity. Furthermore an antidepressant effect is indicated by the overall pharmacological profile of the compounds of the invention.

The compounds of the invention may be administered orally, parenterally and locally (the latter substantially for anti-inflammatory purposes), in a daily dosage of from 0.005 to 50 mg, preferably 0.01–10 mg, per kg body weight.

Mixed with suitable auxiliaries the compounds I may be compressed into solid dosage units, such as pills, tablets and coated tablets or be processed into capsules.

By means of suitable liquids the compounds I can also be applied as an injection preparation in the form of solutions, suspensions or emulsions.

For topical administration the compounds may also be processed into a cream or ointment.

Preferred compounds of the invention are compounds of formula I, in which $R_1$ and $R_2$ are hydrogen or methyl and/or the benzonucleus has been substituted by one or two halogen and/or $R_3$ stands for hydroxy, a lower aliphatic acyloxy group (1–8 C) or a lower araliphatic acyl group, such as benzoyl.

STARTING PRODUCTS

The preparation of 4-exo and 4-endo-hydroxy as well as 4-exo- and 4-endo-benzyloxy-8-chloro-benzo(b)bicyclo[3.3.1]nonen-11-one is described starting from 6-chloro-2-tetralone. Other starting products according to formula II are prepared in a similar manner.

A. 6-chloro-2-tetralone pyrrolidine enamine

A solution of 6-chloro-2-tetralone (260 g) in benzene (1.5 l) and pyrrolidine (208 ml) was refluxed under nitrogen for 2.5 h using a Dean and Stark water separator to collect the water formed. The reaction mixture was evaporated to dryness under reduced pressure, venting with nitrogen at the end of the distillation. The residue was triturated with hexane to give 6-chloro-2-tetralone pyrrolidineenamine (276 g; 82%) m.p. 121°–122° C.

B. 8-chloro-4-hydroxy-benzo(b)bicyclo[3.3.1]nonen-11-one

B.1. 6-chloro-2-tetralone pyrrolidine enamine (390 g) was added portionwise during 10 min. to a stirred solution of acrolein (214 ml) in methylene dichloride (3.0 l) cooled to −50° to −55° C. The reaction mixture was stirred for 30 min. at −50° to −55° C., then the temperature was allowed to rise to +5° during 3 h. Water (420 ml) was added, followed by 5N hydrochloric acid (400 ml) and the resulting biphase mixture was stirred at room temperature for 2 h and set aside overnight. The layers were separated and the aqueous layer was extracted with methylene dichloride. The methylene dichloride extracts were washed with 1N hydrochloric acid, aqueous brine, dried and evaporated to dryness to give a mixture (approx. 60:40) of 8-chloro-4-exo- and 8-chloro-4-endo-hydroxy-benzo(b)bicyclo[3.3.1]nonen-11-one as an oil (371 g).

B.2. Acrolein (389 ml) was added to a stirred solution of 6-chloro-2-tetralone (738 g) in tetrahydrofuran (738 ml) and triethylamine (738 ml) under a nitrogen atmosphere and the mixture was heated under reflux for 2.5 h. The solvents were distilled off in vacuo and the triethylamine finally removed by azeotropic distillation with toluene (2.75 l) in portions (250 ml).

The crude ketol mixture (810 g) was dissolved in toluene, filtered through alumina, and the eluate evaporated to give a mixture (approx. 60:40) of 8-chloro-4-exo- and 8-chloro-4-endo-hydroxy-benzo(b)bicyclo[3.3.1]nonen-11-one as an oil (792 g).

C. 4-Exo- and 4-endo-benzoyloxy-8-chloro-benzo(b)bicyclo[3.3.1]nonen-11-one

A solution of 8-chloro-4-exo- and 8-chloro-4-endo-hydroxybenzo(b)bicyclo[3.3.1]nonen-11-one (52 g) in pyridine (104 ml) was cooled with stirring to 2° and benzoyl chloride (30.5 ml) was added dropwise, keeping the temperature below 10° C. Stirring was continued at 5° to 10° C. for 3.5 h. Water was added to the cooled, stirred mixture to precipitate the product, which was dissolved in methylene dichloride and washed with 2N hydrochloric acid, water to pH 7, dried, and evaporated to give a mixture of 4-exo- and 4-endobenzoyloxy-8-chloro-benzo(b)bicyclo[3.3.1]nonen-11-one (62 g) (approx. 60:40).

A solution of the product in methylene dichloride was filtered through a column of alumina, concentrated, and the residue crystallised from methylene dichloride-cyclohexane to give pure 4-exo-benzoyloxy-8-chloro-benzo(b)bicyclo[3.3.1]nonen-11-one (26 g) m.p. 184°–186° C. The mother liquor was chromatographed over alumina to give a further quantity (7.5 g) of pure 4-exo-benzoyloxy-8-chloro-benzo(b)bicyclo[3.3.1]nonen-11-one and pure 4-endo-benzoyloxy8-chloro-benzo(b)bicyclo[3.3.1]nonen-11-one (18.5 g) m.p. 120°–122° C.

EXAMPLE I 4-exo-Benzoyloxy-8-chloro-11-antiformamido-benzol(b)bicyclo [3.3.1]nonone.

A suspension of 4-exo-benzoyloxy-8-chloro-benzo(b)bicyclo [3.3.1]nonen-11-one (33.5 g) in a mixture of formamide (134 ml) and formic acid (67 ml) is boiled under reflux for 2.5 h. After cooling the mixture, water is added and the solid is filtered off, washed with water and dried (32.5 g). The product is crystallised from methylene dichloride/methanol giving 4-exo-benzoyloxy-8-chloro-11-anti-formamido-benzo(b)bicyclo 3.3.1]nonene as prisms (28.5 g) m.p. 224°–226° C.

EXAMPLE II 4-endo-Benzoyloxy-8-chloro-11-formamido-benzo(b)bicyclo[3.3.1]nonene A stirred suspension of 4-endo-benzoyloxy-8-chloro-benzo(b)bicyclo[3.3.1]nonen-11-one (18.5 g) in a mixture of formamide (74 ml) and formic acid (37 ml) is heated under reflux for 2.5 h. After cooling the mixture, water is added and the gum is dissolved in methylene dichloride, washed neutral and chromatographed over silica gel to give 4-endo-benzoyloxy-8-chloro-11-anti-formamido-benzo(b)bicyclo[3.3.1]nonene (7 g) as prisms m.p. 150°–152° and 4-endo-benzoyloxy-8-chloro-11-synformamido-benzo(b)bicyclo[3.3.1]nonene as an almost colourless gum (3.5 g).

EXAMPLE III

4-Acetoxy- or 4-benzoyloxy-11-formamido-substituted benzo(b)bicyclo[3.3.1]nonene Starting from the desired 4-acyloxy-benzo(b)bicyclo[3.3.1]nonen-11-one compound, unsubstituted or substituted at the benzo ring, the following 11-formamido compounds are prepared in the same manner as described in Examples I and II.

4-exo-Acetoxy-8-methoxy-11-anti-formamido-benzo(b)bicyclo[3.3.1]nonene, m.p. 172°–173° C.;

4-exo-Benzoyloxy-8-bromo-11anti-formamido-benzo(b)bicyclo[3.3.1]nonene, m.p. 229°–230° C.;

4-endo-Benzoyloxy-8-bromo-11-anti-formamido-benzo(b)bicyclo [3.3.1]nonene, (oil)

4-exo-Benzoyloxy-8,9-dichloro-11-anti-formamido-benzo(b) bicyclo[3.3.1]nonene, m.p. 242°–243° C.;

4-endo-p.nitrobenzoyloxy-9-chloro-11-anti-formamido-benzo(b) bicyclo[3.3.1]nonene, m.p. 142°–149° C.;

4-endo-p.nitrobenzoyloxy-9-chloro-11-syn-formamido-benzo(b) bicyclo[3.3.1]nonene, m.p. 197°–200° C.;

4-exo-Acetoxy-11-anti-formamido-benzo(b)bicyclo[3.3.1]nonene, m.p. 121°–122° C.;

4-exo-Acetoxy-11-syn-formamido-benzo(b)-bicyclo[3.3.1]nonene, m.p. 182°–184° C.;

4-exo-Acetoxy-8-chloro-9-CF$_3$-11-anti-formamido-benzo(b)bicyclo[3.3.1]nonene.

EXAMPLE IV 4-exo-hydroxy-8-chloro-11-anti-amino-benzo(b)bicyclo[3.3.1]nonene. HCl A suspension of 4-exo-benzoyloxy-8-chloro-11-anti-formamido-benzo(b)bicyclo[3.3.1]nonene (8 g) in ethanol (80 ml) and 10M potassium hydroxide solution (14 ml) is heated under reflux for 4 h during which time a solution is obtained. After cooling, aqueous brine is added to precipitate the amine which is filtered off, washed with water and dried to give 4-exo-hydroxy-8-chloro-11-anti-amino-benzo(b)bicyclo[3.3.1]nonene as prisms (5 g). The amine (4.3 g) is dissolved in ethanol/toluene and converted to the hydrochloride by addition of a solution of hydrogen chloride gas in ether. Crystallisation from isopropanol gives pure 4-exo-hydroxy-8-chloro-11-anti-amino-benzo(b)bicyclo[3.3.1]nonene hydrochloride (4.1 g) m.p. 182°–194° (decomp.).

In the same manner are prepared:

4-exo-hydroxy-8-methoxy-11-anti-amino-benzo(b)bicyclo[3.3.1]nonene. HCl.

4-exo-hydroxy-8-bromo-11-anti-amino-benzo(b)bicyclo[3.3.1] nonene.HCl.

4-endo-hydroxy-8-bromo-11-anti-amino-benzo(b)bicyclo[3.3.1]nonene.HCl.

4-exo-hydroxy-8,9-dichloro-11-anti-amino-benzo(b)bicyclo [3.3.1]nonene.HCl.

4-endo-hydroxy-8,9-dichloro-11-anti-amino-benzo(b)bicyclo [3.3.1]nonene.HCl.

4-endo-hydroxy-8,9-dichloro-11-syn-amino-benzo(b)bicyclo [3.3.1]nonene.HCl.

4-exo-hydroxy-11-anti-amino-benzo(b)bicyclo[3.3.1]nonene.HCl;

4-exo-hydroxy-8-methyl-11-anti-amino-benzo(b)bicyclo[3.3.1]nonene.HCl.   4-exo-hydroxy-8-chloro-9-

CF$_3$-11-anti-amino-benzo(b)bicyclo[3.3.1-]nonene.HCl.
4-exo-hydroxy-8-hydroxy-8-nitro-11-anti-amino-benzo(b)bicyclo[3.3.1] nonene.HCl.

EXAMPLE V 4-hydroxy-8-chloro-11-methylamino-benzo(b)bicyclo[3.3.1]nonene.HCl.

A solution of 4-exo-benzoyloxy-8-chloro-11-anti-formamido-benzo(b)bicyclo[3.3.1]nonene (7.25 g) in dry tetrahydrofuran (110 ml) is added dropwise to a stirred suspension of lithium aluminium hydride (2.0 g) in dry tetrahydrofuran (40 ml) and the mixture is stirred under reflux for 5 h. After the addition of water, the inorganic solids are filtered off. The filtrate is concentrated, toluene added and the solution is evaporated in vacuo to give 4-exo-hydroxy-8-chloro-11-anti-methylamino-benzo(b)bicyclo[3.3.1]nonene (6.5 g) as a gum, which is dissolved in methylene dichloride and converted to the hydrochloride by addition of a saturated solution of hydrogen chloride gas in ether. Crystallisation from methylene dichloride/ethyl acetate gives pure 4-exo-hydroxy-8-chloro-11-anti-methylamino-benzo(b)bicyclo[3.3.1]nonene hydrochloride as prisms (4.2 g) m.p. <190° C. (decomp.).

In the same manner 4-endo-hydroxy-8-chloro-11antimethylamino-benzo(b)bicyclo[3.3.1]nonene hydrochloride, m.p. 262°–268° and 4-endo-hydroxy-8-chloro-11-syn-methyl-amino-benzo(b)bicyclo[3.3.1]nonene hydrochloride are prepared starting from the appropriate 4-endo-acetoxy- or benzoyloxy-11-formamido compounds.

EXAMPLE VI

4-Hydroxy-11-methylamino-substituted-benzo(b)bicyclo[3.3.1]nonene

Starting from the desired 4-acetoxy- or 4-benzoyloxy-11-formamido-benzo(b)bicyclo[3.3.1]nonene, unsubstituted at the phenyl ring, or substituted at the phenyl ring with 9-chloro, 8-methoxy, 8-hydroxy, 8-methyl, 8,9-dichloro- or 8-chloro-9-nitro respectively, the following 11-methylamino compounds are prepared in the same manner as described in Example V.

4-exo-Hydroxy-11-anti-methylamino-benzo(b)bicyclo[3.3.1]nonene.
4-endo-Hydroxy-11-anti-methylamino-benzo(b)bicyclo[3.3.1]nonene.
4-exo-Hydroxy-8-methoxy-11-anti-metnylamino-benzo(b)bicyclo [3.3.1]nonene.
4-endo-Hydroxy-8-methoxy-11-anti-methylamino-benzo(b)bicyclo [3.3.1]nonene.
4-endo-Hydroxy-8-methoxy-11-syn-methylamino-benzo(b)bicyclo [3.3.1]nonene.
4(endo), 8-Dihydroxy-11-anti-methylamino-benzo(b)bicyclo[3.3.1]nonene.
4-exo-Hydroxy-8-methyl-11-anti-mmethylamino-benzo(b)bicyclo [3.3.1]nonene.
4-exo-Hydroxy-8,9-dichloro-11-anti-methylamino-benzo(b)bicyclo[3.3.1]nonene.
4-exo-Hydroxy- 9-chloro-11-anti-methylamino-benzo(b)bicyclo[3.3.1]nonene.

EXAMPLE VII

8-Bromo-4-exo-hydroxy-11-anti-methylamino-benzo(b)bicyclo[3.3.1]nonene.HCl

A mixture of 4-exo-benzoyloxy-8-bromo(b)bicyclo[3.3.1]nonen-11-one (6 g) and N-methyl-formamide (18 ml) in formic acid (9 ml) is boiled under reflux for 3 h. The reaction mixture is cooled to room temperature, diluted with water and treated with 2N sodium hydroxide solution to give a yellow gum, which is extracted with methylene dichloride. The methylene dichloride extracts were washed with water, dried and evaporated to give a brown gum (5.97 g). The gum (5.97 g) is dissolved in ethanol (120 ml) and heated under reflux with 10N potassium hydroxide solution (12 ml) for 27 h. The reaction mixture is cooled to room temperature, diluted with brine and extracted with methylene dichloride. The methylene dichloride extracts are washed with water, dried and evaporated in vacuo to give the crude amine as an orange gum (4.23 g), which is dissolved in methylene dichloride and converted to the hydrochloride by addition of a solution of hydrogen chloride gas in ether. Crystallisation from methylene chloride and from methanol-ether gives pure 4-exo-hydroxy-8-bromo-11-anti-methylamino-benzo (b)bicyclo[3.3.1]nonene hydrochloride as colourless crystals (1.30 g), m.p. 264°–270° C.

EXAMPLE VIII 4-exo-acetoxy-8-chloro-11-anti-methylamino-benzo(b)bicyclo[3.3.1]nonene.HCl.

A solution of 4-exo-hydroxy-8-chloro-11-anti-methylamino-benzo(b)bicyclo[3.3.1]nonene (4 g) in a mixture of perchloric acid (6 ml), acetic anhydride (10 ml) and glacial acetic acid (20 ml) is set aside for 1 h. The solution is poured into ice-water, solid potassium carbonate added until alkaline and the product is extracted into methylene dichloride, washed to neutrality, dried and evaporated to dryness to give 4-exo-acetoxy-8-chloro-11-anti-methylamino-benzo(b)bicyclo[3.3.1-]nonene (4.7 g) as a gum. The product is dissolved in methylene dichloride and filtered through acid-washed alumina. The eluate is concentrated and a saturated solution of hydrogen chloride gas in ether is added to precipitate the hydrochloride (3.65 g), crystallisation of which from methanol-ethyl acetate yields 4-exo-acetoxy-8-chloro-11-anti-methylamino-benzo(b)bicyclo[3.3.1]nonene hydrochloride as prisms (3.1 g) m.p. 256° C.

In a similar manner the following compounds are prepared: 4-exo-acetoxy-8-chloro-11-anti-amino-benzo(b)bicyclo[3.3.1]nonene.HCl, m.p. 256° C.;
4-endo-acetoxy-8-chloro-11-amino-benzo(b)bicyclo[3.3.1]nonene.HCl, m.p. 259°–263° C.;
4-exo-acetoxy-8,9-dichloro-11-anti-methylamino-benzo(b)bicyclo[3.3.1]nonene.HCl, m.p. 247°–253° C.

EXAMPLE IX 4-exo-benzoyloxy-8-chloro-11-anti-amino-benzo(b)bicyclo[3.3.1]nonene.HCl Benzoyl chloride (2.3 ml) is added dropwise to a solution of 4-exo-hydroxy-8-chloro-11-anti-amino-benzo(b)bicyclo[3.3.1]nonene (4.8 g) in trifluoracetic acid (20 ml) and the mixture is stirred at room temperature for 7 h. then poured on to ice. Solid sodium carbonate is added until alkaline and the product is extracted into ethyl acetate. The extract is washed with 2 M NaOH, and water to pH 7, then dried and evaporated to give a gum (5.0 g). Crystallisation from ether gives 4-exo-benzoyloxy-8-chloro-11-anti-amino-benzo(b)bicyclo[3.3.1-]nonene (3.2 g).

Treatment of the crystalline product in methylene dichloride with a saturated solution of hydrogen chloride gas in ether gives 4-exo-benzoyloxy-8-chloro-11-anti-amino-benzo(b)bicyclo[3.3.1]nonene.HCl, m.p. 213°–220° C.

EXAMPLE X

By treatment of the 4-hydroxy-11-amino- and 11methylamino compounds with the appropriate acylhalide, the following compounds are prepared in a manner, similar to that described in example IX.

4-exo-benzoyloxy-8-chloro-11-anti-methylamino-benzo(b)bicyclo[3.3.1]nonene.HCl.
4-exo-(2,2-dimethylpropionyloxy)-8-chloro-11-anti-aminobenzo(b)bicyclo[3.3.1]nonene.HCl.
4-endo-benzoyloxy-8-methoxy-11-syn-methylamino-benzo(b)bicyclo[3.3.1]nonene.HCl.
4-exo-benzoyloxy-8-bromo-11-anti-amino-benzo(b)bicyclo[3.3.1]nonene.HCl.

EXAMPLE XI 4-exo-hydroxy-8,9-dichloro-11anti-dimethylamino-benzo(b)bicyclo[3.3.1]nonene.HCl A solution of 4-exo-hydroxy-8,9-dichloro-11-anti-aminobenzo(b)bicyclo[3.3.1]nonene (16.6 g) in a mixture of formic acid (16.6 ml) and formalin (15.5 ml) is boiled under reflux for 2 h., diluted with water and an excess of potassium hydrogen carbonate solution and extracted with methylene dichloride. The extract is washed neutral with water, dried and evaporated and the residue crystallised from ether to give 4-exo-hydroxy-8,9-dichloro-11-anti-dimethylaminobenzo(b)bicyclo[3.3.1]nonene (16.2 g), m.p. 133.5°–135°. The product is dissolved in methylene chloride and treated with a solution of hydrogen chloride in ether to give the hydrochloride, m.p. 248°–273° C.

The same compound is obtained by refluxing a mixture of 4-exo-benzoyloxy-8,9-dichloro-benzo(b)bicyclo[3.3.1]nonene-11-one and dimethylformamide in formic acid in a similar manner as described in Example VII.

EXAMPLE XII

4-Hydroxy-11-dimethylamino-benzo(b)bicyclo[3.3.1]nonenes.

Starting from the desired 4-hydroxy-11-amino-benzo(b)bicyclo[3.3.1]nonene, unsubstituted at the phenyl ring, or substituted at the phenyl ring with 8,9-dichloro, 8-methoxy, 8-hydroxy, 9-chloro, 8-chloro and 8,10-dichloro respectively, the following 11-dimethylamino compounds are prepared in the manner described above.

4-exo-hydroxy-11-anti-dimethylamino-benzo(b)bicyclo[3.3.1]nonene.HCl,
4-exo-hydroxy-8-methoxy-11-anti-dimethylamino-benzo(b)bicyclo[3.3.1]nonene.HCl,
4-endo-hydroxy-8,9-dichloro-11-anti-dimethylamino-benzo(b)bicyclo[3.3.1]nonene.HCl,
4-endo-hydroxy-8,9-dichloro-11-syn-dimethylamino-benzo(b)bicyclo[3.3.1]nonene.HCl,
4(exo),8-dihydroxy-11-anti-dimethylamino-benzo(b)bicyclo[3.3.1]nonene.HCl,
4-exo-hydroxy-8-chloro-11-anti-dimethylamino-benzo(b)bicyclo[3.3.1]nonene.HCl,
4-endo-hydroxy-8-chloro-11-anti-dimethylamino-benzo(b)bicyclo[3.3.1]nonene.HCl,
4-endo-hydroxy-8-chloro-11-syn-dimethylamino-benzo(b)bicyclo[3.3.1]nonene.HCl,
4-exo-hydroxy-9-chloro-11-anti-dimethylamino-benzo(b)bicyclo[3.3.1]nonene.HCl,
4-exo-hydroxy-8,10-dichloro-11-syn-dimethylamino-benzo(b)bicyclo[3.3.1]nonene.HCl.

EXAMPLE XIII 4-exo-Acetoxy-8,9-dichloro-11-anti-dimethylamino-benzo(b)bicyclo[3.3.1]nonene.HCl.

Acetylation of 4-exo-hydroxy-8,9-dichloro-11-anti-dimethylamino-benzo(b)bicyclo[3.3.1]nonene (4.0 g) with acetic anhydride (8 ml) and pyridine (8 ml) at room temperature gives 4-exo-acetoxy-8,9-dichloro-11-anti-dimethylamino-benzo(b)bicyclo[3.3.1]nonene (4.4 g), m.p. 122.5°–124°. This is dissolved in methylene chloride and treated with a solution of hydrogen chloride in ether to give the hydrochloride, m.p. 234°–279°.

The following compounds are acylated in a similar manner
4-endo-acetoxy-8,9-dichloro-11-anti-dimethylamino-benzo(b)bicyclo[3.3.1]nonene.HCl,
4-exo-phenylacetoxy-8,9-dichloro-11-anti-dimethylamino-benzo(b)bicyclo[3.3.1]nonene.HCl,
4-exo-benzoyloxy-8,9-dichloro-11-anti-dimethylamino-benzo(b)bicyclo[3.3.1]nonene.HCl,
4-exo-heptanoyloxy-8,9-dichloro-11-anti-dimethylamino-benzo(b)bicyclo[3.3.1]nonene.HCl,
4-exo-(2,2-dimethylpropionyloxy)-8,9-dichloro-11-anti-dimethylamino-benzo(b)bicyclo[3.3.1]nonene.HCl.

EXAMPLE XIV

Esters of 4-hydroxy-11-dimethylamino-benzo(b)bicyclo[3.3.1]nonene derivatives.

Starting from the desired 4-hydroxy-11-dimethylamino-benzo(b)bicyclo[3.3.1]nonene, unsubstituted at the phenyl ring, or substituted at the phenyl ring with 8-methoxy, 8-bromo, 8-chloro and 8-methyl respectively, the following esters of 4-hydroxy-11-dimethylamino compounds are prepared in the manner described above.

4-exo-acetoxy-11-anti-dimethylamino-benzo(b)bicyclo[3.3.1]nonene.HCl.
4-exo-benzoyloxy-11-anti-dimethylamino-benzo(b)bicyclo[3.3.1]nonene.HCl.
4-exo-(2,2-dimethylpropionyloxy)-11-anti-dimethylamino-benzo(b)bicyclo[3.3.1]nonene.HCl.
4-exo-(1-phenylpropionyloxy)-11-anti-dimethylamino-benzo(b)bicyclo[3.3.1]nonene.HCl.
4-exo-cinnamoyloxy-11-anti-dimethylamino-benzo(b)bicyclo[3.3.1]nonene.HCl.
4-exo-decanoyloxy-11-anti-dimethylamino-benzo(b)bicyclo[3.3.1]nonene.HCl.
4-exo-acetoxy-8-bromo-11-anti-dimethylamino-benzo(b)bicyclo[3.3.1]nonene.HCl.
4-endo-benzoyloxy-8-chloro-11-syn-dimethylamino-benzo(b)bicyclo[3.3.1]nonene.HCl.
4-exo-(2,2-dimethylpropionyloxy)-8-chloro-11-anti-dimethylamino-benzo(b)bicyclo[3.3.1]nonene.HCl.
4-endo-benzoyloxy-8-chloro-11-anti-dimethylamino-benzo(b)bicyclo[3.3.1]nonene.HCl.
4-exo-acetoxy-8-chloro-11-anti-dimethylamino-benzo(b)bicyclo[3.3.1]nonene.HCl.
4-exo-benzoyloxy-8-chloro-11-anti-dimethylamino-benzo(b)bicyclo[3.3.1]nonene.HCl.

EXAMPLE XV 4-exo-acetoxy-11-anti-acetamido-benzo(b)bicyclo[3.3.1]nonene 4-exo-hydroxy-11-anti-amino-benzo(b)bicyclo[3.3.1]nonene (20 g) is suspended in acetic anhydride (40 ml) and the mixture stirred at room temperature for 1 hour, and then poured into water. The solid is collected and dried to give 4-exo-acetoxy-11-anti-acetamido-benzo(b)bicyclo[3.3.1]nonene (12.6 g), m.p. 213°-214°.

In the same manner is prepared with (phenyl)propionylchloride:
4-exo-phenylpropionyloxy-11-anti-phenylpropionylamido-benzo(b)bicyclo[3.3.1]nonene,
4-exo-propionyloxy-11-anti-propionylamido-benzo(b)bicyclo[3.3.1]nonene.

A stirred suspension of 4-exo-benzoyloxy-8-chloro-11-anti-amino-benzo(b)bicyclo[3.3.1]nonene in acetic anhydride results in the same manner as described above in 4-exo-benzoyloxy-8-chloro-11-anti-acetamido-benzo(b)bicyclo[3.3.1]nonene.

A stirred mixture of 4-exo-benzoyloxy-8-chloro-11-anti-amino-benzo(b)bicyclo[3.3.1]nonene and benzoylchloride in toluene results in: 4-exo-benzoyloxy-8-chloro-11-anti-benzoylamido-benzo(b)bicyclo[3.3.1]nonene.

EXAMPLE XVI 4-exo-hydroxy-11-anti-ethylamino-benzo(b)bicyclo[3.3.1]nonene.HCl To a suspension of LiAlH$_4$ (3.3 g) in dry tetrahydrofuran is added a hot suspension of 4-exo-acetoxy-11-anti-acetamido-benzo(b)bicyclo[3.3.1]nonene (12.5 g) in a mixture of tetrahydrofuran and dioxan (300 ml) and the mixture refluxed for 2 hours. The excess lithium aluminium hydride is destroyed by the addition of water, the mixture filtered and the filtrate evaporated to dryness. The residue is dissolved in ether, treated with a saturated solution of hydrogen chloride in ether and the solid formed is recrystallised from methane-ether to give 4-exo-hydroxy-11-anti-ethylamino-benzo(b)bicyclo[3.3.1]nonene hydrochloride (12 g), m.p. >265°.

In the same manner is prepared:
4-exo-hydroxy-11-anti-phenylpropylamino-benzo(b)bicyclo[3.3.1]nonene.HCl,
4-exo-hydroxy-11-anti-propylamino-benzo(b)bicyclo[3.3.1]nonene,
4-exo-hydroxy-8-chloro-11-anti-ethylamino-benzo(b)bicyclo[3.3.1]nonene,
4-exo-hydroxy-8-chloro-11-anti-cyclopropylmethylamino-benzo(b)bicyclo[3.3.1]nonene,
4-exo-hydroxy-8-chloro-11-anti-p-hydroxyphenethylamino-benzo(b)bicyclo[3.3.1]nonene.

EXAMPLE XVII 4-exo-Hydroxy-11-anti-N-methyl-N-(3-methyl-but-2-enyl)-amino-benzo(b)bicyclo[3.3.1]nonene hydrochloride To a stirred suspension of 4-exo-hydroxy-11-anti-methyl-amino-benzo(b)bicyclo[3.3.1]nonene (5.5 g) and potassium bicarbonate (5.0 g) in dimethyl formamide (10 ml) and methylene chloride (1 ml) is added dropwise a solution of 1-bromo-3-methyl-but-2-ene (5.5 ml) in dimethyl formamide (10 ml) whilst maintaining the mixture at room temperature. The reaction mixture is stirred for a further 15 minutes and then poured into water. The product is extracted with methylene dichloride. The extract is washed with water, dried and evaporated to give an oil, which is chromatographed on alumina. Elution with benzene gives an oil (5 g) which is dissolved in ether and treated with a saturated solution of hydrogen chloride in ether. The solid formed is recrystallised from methanol-ether to give 4-exo-hydroxy-11-anti-N-methyl-N-(3-methyl-but-2-enyl)-amino-benzo(b)bicyclo[3.3.1]nonene hydrochloride (3.1 g), m.p. 258°-259°.

EXAMPLE XVIII

In an analogous manner as described in Example I various benzo(b)bicyclo[3.3.1]nonene derivatives are prepared by reacting 4-exo-benzoyloxy-8-chloro-benzo(b)bicyclo[3.3.1]nonen-11-one with the desired amine of formula III in the presence of formic acid or with the amine salt of formic acid, whether or not dissolved in a suitable inert solvent. In this manner are prepared:
4-exo-benzoyl-8-chloro-11-anti-morpholino-benzo(b)bicyclo[3.3.1]nonene,
4-exo-benzoyl-8-chloro-11-anti-piperidino-benzo(b)bicyclo[3.3.1]nonene,
4-exo-benzoyl-8-chloro-11-anti-pyrrolidino-benzo(b)bicyclo[3.3.1]nonene.

EXAMPLE XIX

Various 4-hydroxy-benzo(b)bicyclo[3.3.1]nonene-11-oxime derivatives are reduced with sodium in isopropanol to give the corresponding primary amines I. The oximes are obtained by reaction of 4-(endo or exo)-benzoyloxy-benzo(b)bicyclo[3.3.1]nonen-11-one derivatives with hydroxylamine.HCl in sodium hydroxide and ethanol. The following compounds are prepared:
4-exo-hydroxy-8-methoxy-11-anti-amino-benzo(b)bicyclo[3.3.1]nonene.HCl, m.p. 256°-258° C.,
4-exo-hydroxy-8,9-dichloro-11-anti-amino-benzo(b)bicyclo [3.3.1]nonene.HCL, m.p. 286°-300° C.,
4-exo-hydroxy-11-anti-amino-benzo(b)bicyclo [3.3.1]nonene.HCl, sublimation > 265° C.

EXAMPLE XX

In the same manner as described in Example I the following compounds are prepared by refluxing the appropriate starting ketone in a mixture of formic acid and formamide or dimethylformamide respectively:
4-exo-p.nitrobenzoyloxy-9-chloro-11-anti-formamido-benzo(b)bicyclo[3.3.1]nonene.HCl, m.p. 269°-272° C.;
4-exo-p.nitrobenzoyloxy-8-nitro-9-chloro-11-anti-formamido-benzo(b)bicyclo[3.3.1]nonene.HCl, m.p. 276°-279° (dec.);
4-exo-p.nitrobenzoyloxy-9-chloro-10-nitro-11-anti-formamido-benzo(b)bicyclo[3.3.1]nonene.HCl, m.p. 253°-262° C. (dec.);
4-endo-p.nitrobenzoyloxy-8-nitro-9-chloro-11-anti-formamido-benzo(b)bicyclo[3.3.1]nonene.HCl, m.p. 229°-231° C.;
4-exo-hydroxy-8-chloro-9-nitro-11-anti-formamido-benzo(b)bicyclo[3.3.1]nonene.HCl, m.p. 248° C.;
4-exo-methoxy-8-chloro-11-anti-dimethylamino-benzo(b)bicyclo[3.3.1]nonene, (oil);
4-exo-hydroxy-8-t.butyl-11-anti-dimethylamino-benzo(b)bicyclo[3.3.1]nonene (oil);
4-exo-decanoyloxy-8-chloro-11-anti-dimethylamino-benzo(b)bicyclo[3.3.1]nonene, HCl.

We claim:

1. A compound of the formula:

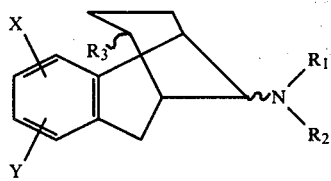

or a pharmaceutically acceptable salt or nitrogen oxide thereof, in which
$R_1$ and $R_2$ stand for hydrogen, alkyl of 1 to 6 carbon atoms;
$R_3$ is a free or etherified hydroxy; and
X and Y stand for hydrogen, hydroxy, halogen, alkyl of 1 to 6 carbon atoms, alkoxy of 1 to 6 carbon atoms, nitro and $CF_3$.

2. A compound according to claim 1 of the formula:

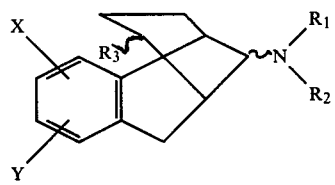

or a pharmaceutically acceptable salt thereof, in which
X or Y represents halogen, the other being hydrogen or halogen,
$R_1$ and $R_2$ represent hydrogen or methyl and
$R_3$ represents hydroxy.

3. A compound of the formula:

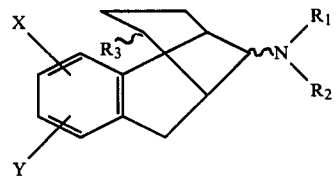

or a pharmaceutically acceptable salt or nitrogen oxide thereof, wherein $R_1$ and $R_2$ are either of hydrogen or alkyl of 1 to 6 carbon atoms;
$R_3$ is etherified hydroxy; and
X and Y are members selected from the group consisting of hydrogen, hydroxy, halogen, alkyl of 1 to 6 carbon atoms, alkoxy of 1 to 6 carbon atoms, nitro, and $CF_3$.

4. The compound of claim 3 wherein $R_3$ is selected from the group consisting of a 1 to 6 carbon atom aliphatic ether, a 5 to 10 carbon atom cycloaliphatic ether, phenoxy, substituted phenoxy wherein the substituent is selected from the group consisting of 1 to 4 carbon atom alkyl, 1 to 4 carbon atom alkoxy, halogen, and nitro; and tetrahydropyranylether.

5. The compound of claim 4 wherein $R_3$ is methoxy.

6. The compound of claim 3 which is 4-exo-methoxy-8-chloro-11-anti-dimethylamino-benzo(b)bicyclo[3.3.1-]nonene.

7. A compound of the formula:

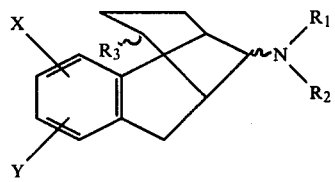

or a pharmaceutically acceptable salt or nitrogen oxide thereof wherein
$R_1$ and $R_2$ are either of hydrogen or alkyl of 1 to 6 carbon atoms;
$R_3$ is free hydroxy; and
X and Y are both halogen.

8. The compound of the formula:

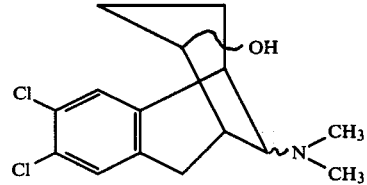

or a pharmaceutically acceptable salt thereof.

* * * * *